United States Patent [19]

Omura et al.

[11] Patent Number: 4,886,884
[45] Date of Patent: Dec. 12, 1989

[54] DERIVATIVES FROM CERVINOMYCIN BASED ANTIBIOTICS

[75] Inventors: Satoshi Omura; Akira Nakagawa, both of Tokyo; Yuzuru Iwai, Chiba, all of Japan

[73] Assignee: The Kitazato Institute, Tokyo, Japan

[21] Appl. No.: 124,786

[22] PCT Filed: Feb. 17, 1987

[86] PCT No.: PCT/JP87/00103

§ 371 Date: Oct. 19, 1987

§ 102(e) Date: Oct. 19, 1987

[87] PCT Pub. No.: WO87/05023

PCT Pub. Date: Aug. 27, 1987

[30] Foreign Application Priority Data

Feb. 17, 1986 [JP] Japan .................................. 61-32387

[51] Int. Cl.⁴ .......................................... C07D 498/12
[52] U.S. Cl. ...................................... 546/36
[58] Field of Search .......................................... 546/36

[56] References Cited

U.S. PATENT DOCUMENTS 4,814,449 3/1989 Chang-ging et al. .................. 546/36

FOREIGN PATENT DOCUMENTS 0246091 5/1987 European Pat. Off. .

OTHER PUBLICATIONS

Gurevich et al., "Structure of Albofungin", Tethrahed, Lett. No. 18 pp. 1751-1754, (1972).
Dobler et al., "Metabolites of Microorganisms", Helv. Chim. Acta. vol. 60 No. 19 pp. 178-185 (1977).
Omura et al., "Struct. of Gervinomycin", Chem. Abs. vol. 106: 2725 v, p. 443 (1987).
Qi et al., "Prep. of Antibiotic and Antitumor Subst.", Chem. Abs. vol. 108: 130060d, p. 602 (1988).
Journal of the American Chemical Society, 108:6088-6089 (Sep., 1986).

The Journal of Antibiotics, 39:1636-1638 (Nov. 1986).

Primary Examiner—Mukund J. Shah
Assistant Examiner—Andrew C. Rozycki
Attorney, Agent, or Firm—Sughrue, Mion, Zinn, Macpeak & Seas

[57] ABSTRACT

The present invention is to provide a novel cervinomycin derivative represented by formula

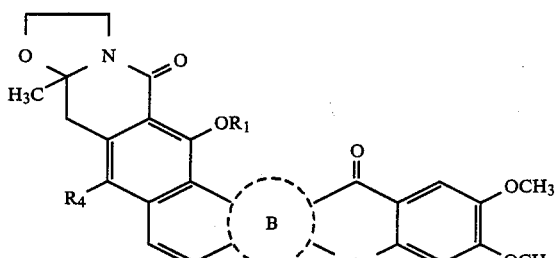

wherein ring B represents

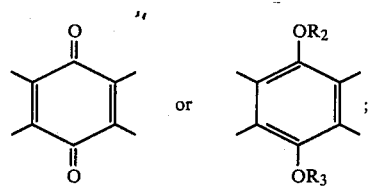

at least one of $R_1$, $R_2$ and $R_3$ represents an acyl group or an alkyl group and the others represent a hydrogen atom; and $R_4$ is a hydrogen atom or an alkyl group, and a process for producing said derivatives. The present derivative is free from the problems of the conventional cervinomycin, i.e., the low solubility in various solvents, high toxicity, and low activity against Gram-positive bacteria.

1 Claim, No Drawings

DERIVATIVES FROM CERVINOMYCIN BASED ANTIBIOTICS

TECHNICAL FIELD

The present invention relates to novel derivatives of cervinomycin based antibiotics and a process for producing the same.

BACKGROUND TECHNIQUE

Several compounds have been known as antibiotics having xanthone in their basic structure and they include: albofungin (=Kanchanomycin, BA-180265*, P-42-1**) as reported in *Tetrahedron Letters*, 18, 1751 (1972), *Antimicrob. Agent & Chemoth.*, 767 (1962)*, and *J. Antibiotics.*, 26, 65 (1973)**, lysolipin I as reported in *Arch. Microbid.*, 106, 175 (1975) and *Helv. Chim. Acta.*, 60, 178 (1977); antibiotic AM-5344-$A_1$ as disclosed in Japanese Patent Application (OPI) No. 9690/1983 (this antibiotic was later designated Cervinomycin $A_1$); and antibiotic AM-5344-$A_2$ as disclosed in Japanese Patent Application (OPI) No. 102897/1982 (this antibiotic was later designated Cervinomycin $A_2$) now U.S. Pat. No. 4,666,715.

The present inventors investigated the solubility and toxicity of the cervinomycin compounds mentioned above and found that they were very poorly soluble in a variety of solvents, had strong toxicity and that they exhibited weak activity against Mycoplasmas and certain Gram-positive bacteria.

Under these circumstances, it is necessary for the purposes of medical treatment of human and animal subjects to develop novel derivatives of cervinomycin that have enhanced solubility, improved antibacterial activity and reduced toxicity.

DISCLOSURE OF THE INVENTION

Therefore, the present invention analyzed the structures of Cervinomycin $A_1$ and $A_2$ and undertook synthesis of various derivatives thereof with a view to solving the aforementioned problems of these antibiotics. As a result, the present invention found that novel cervinomycin derivatives of formula [1] noted below exhibit strong activity against Gram-positive and Gram-negative bacteria, as well as pathogenic microorganisms like mycoplasmas. The derivatives exhibit particularly high activity against mycoplasmas that are the causative organism of Mycoplasma pneumonia, and against a variety of anaerobic organisms. The present inventors also found that these derivatives had enhanced solubility in solvents and that yet their toxicity was markedly reduced as compared with cervinomycins and known related antibiotics having xanthone in their basic structure. The present invention has been accomplished on the basis of these findings.

Accordingly, the present invention is to provide a compound represented by formula (1):

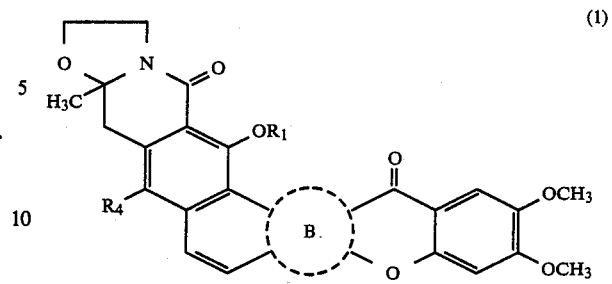

wherein ring B represents

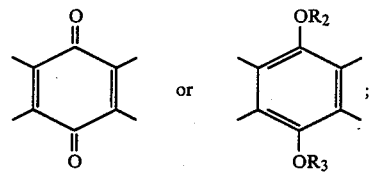

at least one of $R_1$, $R_2$ and $R_3$ is an acyl group or an alkyl group, and the others are a hydrogen atom; and $R_4$ is a hydrogen atom or an alkyl group. The present invention also provides a process for producing such a compound.

Compound [1] of the present invention can be produced by reacting Cervinomycin $A_1$ or $A_2$ with an acylating or alkylating agent in a solvent. According to this reaction, the hydroxyl group in Cervinomycin $A_1$ or $A_2$ having the chemical structure shown below is acylated with an acylating agent or O- or C-alkylated with an alkylating agent.

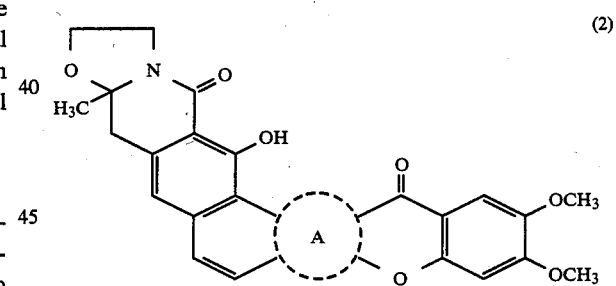

wherein ring A represents

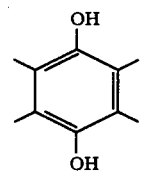

in Cervinomycin $A_1$, and

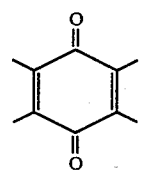

in Cervinomycin A$_2$.

The acylating agent may be selected from among known aliphatic carboxylic acids or reactive derivatives thereof. The term "reactive derivatives" means reactive derivatives of a carboxyl group that are generally used in esterifying a hydroxyl group, and examples of such derivatives include acid halides such as acid chlorides and acid bromides, as well as acid azides, acid anhydrides, mixed acid anhydrides, and active esters. Other acylating agents known in the art may of course be used. If aliphatic carboxylic acids are used as such, condensing agents such as carbodiimides (e.g., N,N'-dicyclohexylcarbodiimide (DCC)) and N,N'-carbonylbisimidazole may be used in combination for achieving acylation.

The alkylating agent may be selected from among known alkylating agents such as alkyl halides (e.g., alkyl iodides and alkyl bromides) and dialkylsulfuric acids.

The acylation or alkylation of the hydroxyl group in Cervinomycin A$_1$ or A$_2$ is carried out in a reaction solvent. A suitable reaction solvent is an organic solvent such as chloroform or pyridine.

The reaction is generally performed in the presence of a catalyst selected from tertiary organic amines such as triethylamine, 4-dimethylaminopyridine, 4-piperidinopyridine and tribenzylamine.

The reaction can be monitored by a suitable technique such as thin-layer chromatography on silica gel or high-performance liquid chromatography, whereby the operator may terminate the reaction after confirming that a maximum yield of the end compound (1) has been produced.

As a result of the reaction, all of the hydroxyl groups in cervinomycin (2) are usually acylated or alkylated but if a cervinomycin having three hydroxyl groups is used as the starting material, compound (1) having only one or two hydroxyl groups acylated or alkylated may result depending upon the type of acylating or alkylating agent used, the presence or absence of a catalyst, the proportion of such agent or catalyst, or upon the duration of reaction time.

The end compound (1) can be recovered from the reaction solution by first pouring it into water, then extracting compound (1) with a non-hydrophilic organic solvent such as ethyl acetate or chloroform. If desired, compound (1) may be further purified with a suitable isolation and purification technique such as column chromatography using a known absorbent such as silica gel.

Compound (1) of the present invention may be used as a pharmaceutical composition that contains it as an active ingredient and which can be administered by any method such as intravenous injection, intramuscular injection, peroral application, rectal application and aerosol application. This composition may be either solid or liquid and can be formulated by routine procedures in any of the dosage forms currently employed in pharmaceutical areas such as sugar-coated tablets, uncoated compressed tablets, gelatin capsules, granules, suppositories, injections, ointments and cream. In addition to the active ingredient, these pharmaceutical compositions may contain common excipients such as talc, gum arabic, lactose, starch, magnesium stearate, cocoa butter, animal and vegetable fats, paraffin derivatives and glycol, as well as a variety of humectants, dispersants, emulsifiers or preservatives.

The dosage of the end compound (1) may be properly determined according to such factors as the severity of the disease to be treated, the age of patient, and the route of administration.

BEST MODE FOR CARRYING OUT THE INVENTION

Example 1

Preparation of triacetyl Cervinomycin A$_1$

Triacetyl Cervinomycin A$_1$:

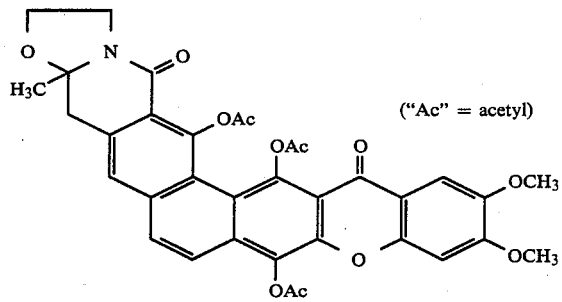

("Ac" = acetyl)

500 mg of Cervinomycin A$_1$ was added to a mixture of 2 ml of acetic anhydride and 15 ml of pyridine. After addition of 1.2 ml of triethylamine, the mixture was stirred at room temperature for 4 days. The reaction mixture was poured into 300 ml of ice water, and the reaction product was extracted with 150 ml of ethyl acetate. The ethyl acetate layer was separated, washed three times with 100 ml portions of water, dried with anhydrous sodium sulfate, and concentrated under vacuum to obtain 630 mg of a brown powder. The powder was purified by silica gel (Kiesel gel G 60) column chromatography (eluting solvent: benzene/acetone (60:1–30:1)) to obtain a pale yellow powder of triacetyl Cervinomycin A$_1$ in an amount of 580 mg (yield: 96%).

Melting point: 280°–283° C.

Specific rotation: $[\alpha]_D^{23}$-132° (c=0.5 chloroform).

UV spectrum: $\lambda_{max}^{CHCl_3}(\epsilon)$; 259 (21,200), 299 (31,180), 355 (10,480), 371 (16,500), 414 (5,700) nm.

Molecular formula: $C_{35}H_{29}NO_{12}$ (from high-resolution mass spectrometry and elemental analysis).

The powder was found to have the chemical structure shown above by analyses of IR, $^1$H and $^{13}$C-NMR spectra.

Example 2

Preparation of monoacetyl Cervinomycin A$_2$

Monoacetyl Cervinomycin A$_2$:

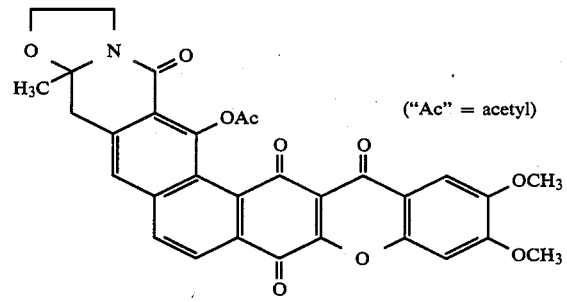

("Ac" = acetyl)

A mixture of 1.6 ml of acetic anhydride and 12 ml of pyridine was added to 500 mg of Cervinomycin $A_2$. After addition of 1.0 ml of triethylamine, the mixture was stirred at room temperature for 3 days. The reaction mixture was poured into 250 ml of ice water and the reaction product was extracted with 150 ml of ethyl acetate. The ethyl acetate layer was separated, washed three times with 100 ml portions of water, dried with anhydrous sodium sulfate, and concentrated under vacuum to obtain 610 mg of a brown powder. The powder was purified by silica gel (Kiesel gel 60) column chromatography (eluting solvent: benzene/acetone (60:1–30:1)) to obtain a pale orange powder of monoacetyl Cervinomycin $A_2$ in an amount of 510 mg (yield: 94%).

Melting point: 295°–300° C.

Specific rotation: $[\alpha]_D^{20}$-497° (c=0.5 chloroform).

UV spectrum: $\lambda_{max}^{CHCl_3}(\epsilon)$; 248 (30,950), 274 (21,400), 307 (25,500), 374 (9,100) nm.

Molecular formula: $C_{31}H_{23}NO_{10}$ (from high-resolution mass spectrometry).

The powder was found to have the chemical structure shown above by analyses of IR, $^1H$ and $^{13}C$-NMR spectra.

Example 3

Preparation of O-methyl-, C-methyl-, and C,O-dimethyl Cervinomycin $A_2$

O—methyl Cervinomycin $A_2$

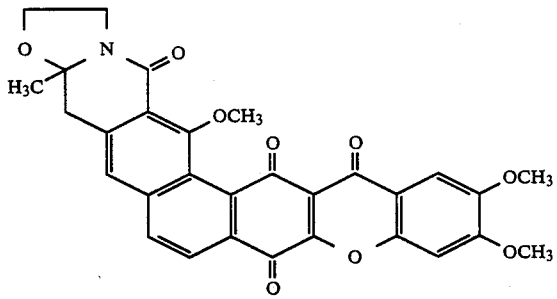

C—methyl Cervinomycin $A_2$

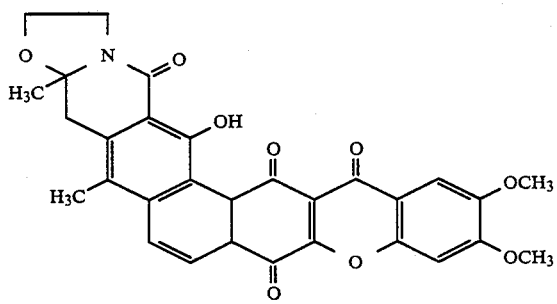

C,O—dimethyl Cervinomycin $A_2$

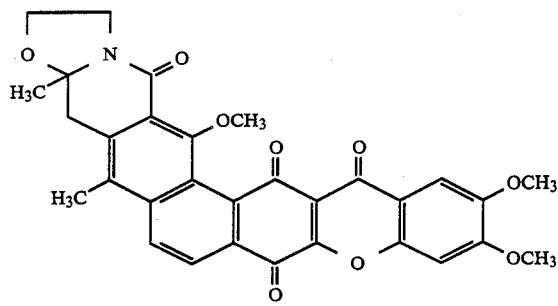

To 500 mg of Cervinomycin $A_2$, 150 ml of a mixture of chloroform and a small amount of methanol was added. After successive addition of 600 mg silver oxide and a large excess of methyl iodide, the mixture was stirred at 30° C. for 3 days. The resulting reaction mixture was filtered to remove the silver oxide and the filtrate was concentrated by evaporation to dryness so as to obtain 570 mg of a brown powder. This powder was purified by silica gel (Kiesel gel 60) column chromatography (eluting solvent: chloroform/methanol/1% aqueous ammonia (60:1:1–40:1:1)). The purified product contained three methylated compounds, which were purified by silica gel thin layer chromatography (developing solvent: chloroform/methanol/1% aqueous ammonia (30:1:1)) to obtain 170 mg of O-methyl Cervinomycin $A_2$, 20 mg of C-methyl Cervinomycin $A_2$, and 120 mg of C,O-dimethyl Cervinomycin $A_2$, each in an orange powder form.

O-methyl Cervinomycin $A_2$

Melting point: >300° C. (with decomposition).
Specific rotation: $[\alpha]_D^{20}$-499° (c=0.5, chloroform).
Molecular formula: $C_{30}H_{23}NO_9$ (from high-resolution mass spectrometry).

C-methyl Cervinomycin $A_2$

Melting point: >260° C. (with decomposition).
Specific rotation: $[\alpha]_D^{20}$-460° (c=0.3, chloroform).
Molecular formula: $C_{30}H_{23}NO_9$ (from high-resolution mass spectrometry)

C,O-dimethyl Cervinomycin $A_2$

Melting point: >255° C. (with decomposition).
Specific rotation: $[\alpha]_D^{20}$-460° (c=0.2, chloroform).
Molecular formula: $C_{31}H_{25}NO_9$ (from high-resolution mass spectrometry).

Based on $^1H$ and $^{13}C$-NMR spectrum analyses, these three methylated derivatives were found to have the chemical structures shown above.

Example 4

Antibacterial activity

Table 1 shows the minimum inhibitory concentrations (MIC) of the compounds shown in Table 1 on different microorganisms that were inoculated in an amount of $1 \times 10^6$ cells/ml and cultivated on heart infusion agar (Difco) at 37° C. for 20 hours, on GAM agar (Nissui) at 37° C. for 20 hours, or on PPLO agar (Eiken) at 37° C. for 7 days.

Further, each of O-methyl-, C-methyl- and C,O-dimethyl Cervinomycin $A_2$ showed an antimicrobial activity that was substantially equal to those of Cervinomycin $A_1$ and $A_2$.

TABLE 1

| Test Organism | MIC (µg/ml) | | | |
|---|---|---|---|---|
| | Cervinomycin $A_1$ | Triacetyl Cervinomycin $A_1$ | Monoacetyl Cervinomycin $A_2$ | Clindamycin |
| (a) Antimicrobial Activity of Cervinomycin $A_1$, Triacetyl Cervinomycin $A_1$, Monoacetyl Cervinomycin $A_2$ and Clindamycin | | | | |
| *Staphylococcus aureus* KB-210 (ATCC 6538P) | 5.0 | 0.16 | 0.31 | 0.16 |
| *Bacillus subtilis* KB-211 (ATCC 6633) | 2.5 | >0.02 | 0.08 | 2.5 |
| *Bacillus cereus* KB-143 (IFO 3001) | 10 | 0.31 | 0.16 | 0.63 |
| *Micrococcus luteus* KB-212 (ATCC 9341) | 5.0 | 0.08 | 0.4 | 0.04 |
| *Escherichia coli* KB-176 (NIHJ JC-2) | >10 | >10 | >10 | >10 |
| *Salmonella typhimurium* KB-20 | >10 | >10 | >10 | >10 |
| *Klebsiella pneumoniae* KB-214 (ATCC 10031) | >10 | >10 | >10 | >10 |
| *Proteus vulgaris* KB-127 (IFO 3167) | >10 | >10 | >10 | >10 |
| *Pseudomonas aeruginosa* KB-115 (IFO 3080) | >10 | >10 | >10 | >10 |
| (b) Antimicrobial Activity of Cervinomycin $A_1$, Triacetyl Cervinomycin $A_1$, Monoacetyl Cervinomycin $A_2$ and Clindamycin | | | | |
| *Clostridium perfringens* (ATCC 13124) | 1.25 | 0.02 | 0.02 | 0.40 |
| *Clostridium difficile* (ATCC 9689) | — | 0.05 | 0.05 | 6.3 |
| *Peptococcus variabilis* KB-235 (ATCC 14955) | 0.62 | 0.02 | — | 0.16 |
| *Bacteroides fragilis* KB-169 (ATCC 23749) | 1.25 | 0.1 | 0.1 | 0.08 |
| *Bifidobacterium bifidum* (ATCC 11146) | — | 0.2 | 0.2 | 0.02 |
| *Mycoplasma gallisepticum* KB-171 (S-6) | 12.5 | 0.156 | 1.25 | 0.62 |
| *Mycoplasma pneumoniae* KB-173 | 12.5 | 0.156 | 0.6 | 0.62 |
| *Acholeplasma laidlawii* KB-174 (PG-8) | 12.5 | 0.312 | 1.25 | 0.62 |

Media: heat infusion agar (Difco) at 37° C. for 20 hrs; GAM agar (Nissui) at 37° C. for 20 hrs; PPLO agar (Eiken) at 37° C. for 7 days
Dose of inoculum: $1 \times 10^6$ cells/ml

Example 5

Acute toxicity

Compounds (1) of the present invention were subjected to an acute toxicity test on ddY mice by oral administration.

| Compounds of the invention | $LD_{50}$ |
|---|---|
| Triacetyl Cervinomycin $A_1$ | 1.62 g/kg |
| Monoacetyl Cervinomycin $A_2$ | 1.80 g/kg |
| Control | |
| Cervinomycin $A_1$ | 0.32 g/kg |

Example 6

Solubility

Compounds (1) of the present invention had the following solubilities in different solvents.

| Compounds of the invention | (unit: mg/ml) | | |
|---|---|---|---|
| | Methanol | Acetic acid | DMSO* |
| Triacetyl Cervinomycin $A_1$ | 1.4 | >25 | >50 |
| Monoacetyl Cervinomycin $A_2$ | 0.3 | 3.0 | 5.0 |
| Cervinomycin $A_1$ | 0.0003 | 0.023 | 0.078 |

Industrial Applicability

As the above data show, compounds (1) of the present invention are novel antibiotic derivatives. In comparison with the starting cervinomycin (2), the compounds show an extremely high activity against Gram-positive bacteria such as Staphylococcus, Bacillus, Micrococcus and Clostridium, Gram-negative bacteria such as Bacteroides, and against Mycoplasma, and they yet have low toxicity and are extremely soluble in various solvents. The antibacterial activity of compounds (1) is comparable to or greater than that of the known antibiotic clindamycin. Therefore, the compounds are useful as therapeutical drugs for infectious diseases that are caused by pathogenic organisms such as the above-mentioned Gram-positive bacteria, Gram-negative bacteria and Mycoplasma and which are exemplified by septicemia caused by infection with Staphylococcus, Clostridium and Bacteroides, and bronchopneumonia caused by infection with Staphylococcus and Mycoplasma.

What is claimed is:
1. A compound represented by formula:
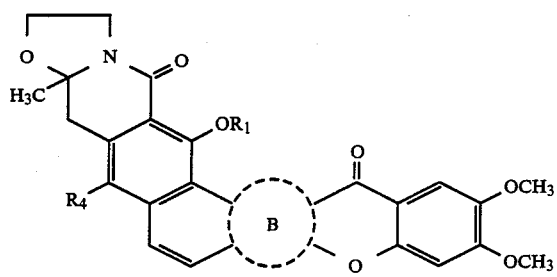
wherein ring B represents
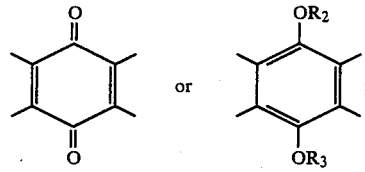
wherein at least one of $R_1$, $R_2$ and $R_3$ represents an acetyl group, and the rest of $R_1$, $R_2$, $R_3$ and $R_4$ represents a hydrogen atom; or at least one of $R_1$, $R_2$, $R_3$ and $R_4$ represents a methyl group and the rest of $R_1$, $R_2$, $R_3$ and $R_4$ represents a hydrogen atom.
* * * * *